(12) United States Patent
Linden et al.

(10) Patent No.: US 7,019,027 B2
(45) Date of Patent: Mar. 28, 2006

(54) 2-AMINO-3-AROYL-4,5 ALKYLTHIOPHENES: AGONIST ALLOSTERIC ENHANCERS AT HUMAN A1 ADENOSINE RECEPTORS

(76) Inventors: Joel M. Linden, 207 Harvest Dr., Charlottesville, VA (US) 22903; Ray A. Ollson, 1126 Bayshore Blvd., #1204, Tampa, FL (US) 33629; Peter J. Scammells, 6 Harrington Avenue-North Balwyn, Victoria (AU) 3104

( * ) Notice: Subject to any disclaimer, the term of this patent is extended or adjusted under 35 U.S.C. 154(b) by 0 days.

(21) Appl. No.: 10/808,093

(22) Filed: Mar. 23, 2004

(65) Prior Publication Data

US 2004/0180948 A1    Sep. 16, 2004

Related U.S. Application Data

(63) Continuation of application No. 10/151,359, filed on May 20, 2002, now Pat. No. 6,713,638.

(60) Provisional application No. 60/292,092, filed on May 18, 2001.

(51) Int. Cl.
*A61K 31/38* (2006.01)
*C07D 333/56* (2006.01)

(52) U.S. Cl. ......................... 514/447; 549/57
(58) Field of Classification Search ................ 514/447; 549/57
See application file for complete search history.

(56) References Cited

U.S. PATENT DOCUMENTS 6,177,444 B1 * 1/2001 Baraldi ....................... 514/301

OTHER PUBLICATIONS

Tinney et al , "Synthesis and Pharmaceutical Evaluation of . . . Thieno . . . Diazepines", CA81:145630, 1974.*

* cited by examiner

*Primary Examiner*—Deborah C. Lambkin
(74) *Attorney, Agent, or Firm*—Kilpatrick Stockton LLP; Charles W. Calkins; J. Clinton Wimbish

(57) ABSTRACT

The present invention relates to a compound of formula (I):

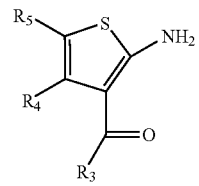

wherein:
$R_3$ is selected from the group consisting of 1-napthyl, 2-napthyl and cycloalkylphenyl; and
$R_4$ and $R_5$ taken together form a ring having from 5 to 10 carbon atoms.

Additionally, the invention provides a therapeutic method for preventing or treating a pathological condition or symptom in a mammal subject, such as a human, wherein increased angiogenesis is desired, comprising administering to a mammal in need of such therapy an effective amount of the aforementioned thiophene selective adenosine $A_1$ allosteric enhancer.

5 Claims, 1 Drawing Sheet

2-AMINO-3-AROYL-4,5 ALKYLTHIOPHENES: AGONIST ALLOSTERIC ENHANCERS AT HUMAN A1 ADENOSINE RECEPTORS

CROSS REFERENCE TO RELATED APPLICATION

This application is a continuation application of U.S. application Ser. No. 10/151,359, filed May 20, 2002, now U.S. Pat. No. 6,713,638 which claims priority to U.S. Provisional application Ser. No. 60/292,092, filed May 18, 2001.

TECHNICAL FIELD OF THE INVENTION

The present invention relates to the use of thiophene derivatives as allosteric enhancers of agonist activity at adenosine $A_1$ receptors.

BACKGROUND OF THE INVENTION

Angiogenesis, the process of new blood vessels formation, is a complex process involving the coordinated interaction of numerous cell types. The critical cells are the endothelial cells, which contain all of the genetic information necessary to form primitive tubes and branches. Other cells, such as smooth muscle cells, mast cells, and macrophages release important modulators of angiogenesis. Hypoxia, decreased blood flow, and released angiogenic substances such as vascular endothelial growth factor (VEGF) can trigger angiogenesis. The process begins with a breakdown of the extracellular matrix, followed by proliferation and migration of endothelial cells into the tissue. Initially the endothelial cells form cords. Later large vacuoles form in the cells, leading to the formation of tubes. The endothelial tubes have a lumen, but are abnormally permeable and leaky until pericytes are recruited to reinforce the new vessels. Several growth factors, most notably VEGF, bFGF, and angiopoetin-1, promote angiogenesis. VEGF, a specific mitogen for endothelial cells, can independently stimulate new vessel growth. However, overexpression of VEGF in developing avian embryos results in large vessels that are leaky, which leads to tissue edema. The coordinated effects of several growth factors may be necessary to stimulate the development of normal new vessels. Hence, finding ways to use upstream modulators in a tissue-specific way may provide a therapeutic advantage over the application of individual growth factors.

VEGF is a direct, or primary, angiogenic factor, meaning that it is able by itself to induce angiogenesis in endothelial cells in vitro or in vivo. Secondary, or indirect, angiogenic factors work by causing cells to release primary factors. Experts fear that using primary factors clinically will cause pathologic angiogenesis in other tissues. Thus, a limitation of using adenosine or other promoters of angiogenesis could be new vessel growth in healthy as well as diseased tissues. Hence, activation of upstream secondary angiogenic stimuli may produce more regulated and normal vascular growth. Additionally, the ability to target angiogenic stimulation to specific tissues would diminish the risk of indiscriminate angiogenesis.

There are widespread clinical applications for the stimulation of the angiogenesis in cardiovascular medicine and ophthalmology. Stimulating new vasculature in ischemic tissues, especially heart and limbs is currently an active clinical endeavor because it could have a major impact on morbidity and mortality from atherosclerosis. Trials in humans have shown the usefulness of VEGF in stimulating collateral vessels to ischemic lower extremities, improving ulcer healing and decreasing limb loss. There are also ongoing clinical trials using VEGF infusions in patients with intractable, inoperable angina pectoris.

Abundant evidence shows that hypoxic or ischemic tissues release adenosine and that adenosine stimulates angiogenesis. Possible mechanisms of vessel growth include increased flow, stimulation of vascular cell proliferation and migration, or stimulation of growth factor secretion. Some of the results obtained in previous studies on adenosine effects in vivo and in vitro have suggested that activation of adenosine $A_2$ receptors ($A_{2A}$ or $A_{2B}$) are responsible for the ability of adenosine to stimulate angiogenesis. The activation of $A_{2B}$ receptors on cultured endothelial cells has been shown to stimulate VEGF release, but $A_1$ adenosine receptor activation seemed to play little or no role. The present invention, however, demonstrates the $A_1$ receptor is more important than has been previously thought. Indeed, the present invention relates to the use of thiophene derivatives as allosteric enhancers of agonist activity at adenosine $A_1$ receptors. Allosteric enhancers of $A_1$ adenosine receptors selectively stimulate angiogenesis in ischemic tissue and not in tissue that has adequate blood flow. This site-specificity represents a major advantage over other angiogeneic agents that are not selective for ischemic tissue.

Adenosine triggers endothelial cell proliferation in cultured cells and angiogenesis in animal models. Adenosine is a logical modulator for the hypoxic stimulation of angiogenesis. It is a metabolite of ATP released from all ischemic or hypoxic tissues, where it acts as a "retaliatory metabolite" to restore normal oxygen delivery, initially by dilating existing blood vessels. Chronic hypoxia has long been considered a driving force for new blood vessel formation. Increased vascular density is seen in humans at high altitudes, in chronically stimulated skeletal muscle, and in rapidly growing tumors. Hypoxia initiates proliferation of cultured endothelial cells that can be blocked by unselective adenosine receptor antagonists. Subtype-selective ligands have been used to tease out the mechanism of adenosine-induced endothelial cell proliferation and migration, but the results have been inconsistent. The chicken chorioallantoic membrane (CAM) model is a suitable vehicle for studying the effect of adenosine on angiogenesis. In this model lowering oxygen concentration stimulates neovascularization, but adenosine has not been consistently angiogenic. Receptor subtype-selective ligands have not previously been tested in the CAM.

Adenosine acts via four types of cell surface, G protein-coupled receptors, $A_1$, $A_{2A}$, $A_{2B}$ and $A_3$. $A_1$ and $A_3$ receptors are the most similar in amino acid sequence and pharmacology. These receptors couple to G proteins from the Gi/Go family and inhibit adenylyl cyclase. Stimulation of $A_1$ and $A_3$ receptors can also activate phospholipase C, presumably via G protein sub-units. $A_{2A}$ and $A_{2B}$ receptors couple to Gs and stimulate adenylyl cyclase, but the $A_{2B}$ receptor can also couple to Gq. In the heart, $A_1$ receptors have negative chronotropic, dromotropic and inotropic effects. The $A_1$ receptor, and perhaps the $A_3$, is also involved in the preconditioning phenomenon, which protects ischemic tissues. Coronary arteries express $A_{2A}$ receptors; their activation results in coronary vasodilation. $A_{2A}$ receptors also occur on leukocytes, where they attenuate the inflammatory response and thereby decrease reperfusion injury. Accordingly, adenosine acts in a number of ways to protect ischemic tissues; it decreases metabolism, increases blood flow, and attenuates inflammatory injury. Adenosine activates $A_{2B}$ receptors on cultured endothelial cells to trigger VEGF release and endothelial mitogenesis. Adenosine also appears to stimulate angiogenesis, but to date no attempt has been made to define the adenosine receptor subtypes involved in the CAM model. Additionally, heretofore, it had not been shown that adenosine stimulates angiogenesis in adult mammalian models. The development of more selective adenosine receptor ligands and cloning of the chicken $A_1$, $A_{2A}$, and $A_3$ receptors have enabled us to identify adenosine receptor subtypes participating in the angiogenic response of CAM.

Allosteric enhancers of receptors are defined as compounds that bind to an allosteric site distinct from the binding site of the endogenous ligand and potentiate responses to agonists. Benzodiazepine anxiolytics and calcium channel blockers are familiar examples of drugs that act allosterically. Allosteric enhancers of adenosine $A_1$ receptors act only on the adenosine-receptor-G protein ternary complex. Accordingly, they have little effect by themselves, but enhance the actions initiated by $A_1$ receptors when increases in endogenous adenosine levels in ischemic tissues increase receptor occupancy.

PD 81,723 (PD) is the archetype of a family of arninothiophenes that were the first described allosteric enhancers of adenosine $A_1$ receptors. These compounds increase binding of [$^3$H]N$^6$-cyclohexyladenosine (CHA) to adenosine $A_1$ receptors and caused a functional enhancement of the effects of adenosine $A_1$ receptor activation in various tissues. PD is selective for adenosine $A_1$ receptors, having no effects on other adenosine receptor subtypes or on other classes of receptors. PD has shown enhancement at $A_1$ receptors of all species tested to date. In the absence of adenosine or $A_1$-selective agonists, the enhancer molecules alone act as very weak antagonists for adenosine receptors. Despite PD demonstrating allosteric enhancer activity, there still remains a need for compounds having improved allosteric enhancer activity.

The administration a compound that promotes angiogenesis can be an effective method for treating stroke, heart disease, peripheral vascular disease. The administration of such compound can also be an effective method for treating cardiac arrhythmias, chronic pain and inducing sleep. The ability of the improved allosteric enhancers described herein to promote angiogenesis in two animal model systems, the chicken chorioallantoic membrane model and the rat mesenteric model, demonstrates that allosteric enhancers of the adenosine $A_1$ receptor enhance the ability of adenosine to promote new vessel growth.

Accordingly, the present invention provides novel thiophene derivatives to be used as improved agonist allosteric enhancers at adenosine $A_1$ receptor.

Additionally, the present invention provides an original therapeutic method for preventing or treating a pathological condition or symptom in a mammalian subject, such as a human, wherein increased angiogenesis is desired, by administering to a mammal in need of such therapy an effective amount of the aforementioned adenosine $A_1$ receptor allosteric enhancer.

SUMMARY OF THE INVENTION

One aspect of the present invention is a compound of Formula I:

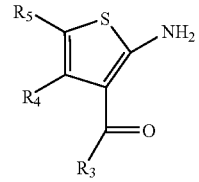

wherein $R_3$ is selected from the group consisting of 1-napthyl, 2-napthyl and cycloalkyl-phenyl; and
$R_4$ and $R_5$ are taken together to form a ring having 5 to 10 carbon atoms.

A second aspect of the present invention is a method of allosterically enhancing adenosine $A_1$ receptors in a mammal, including a human, by the administration to the mammal of an amount of a compound of Formula I sufficient to enhance actions mediated by adenosine receptors.

A third aspect is a pharmaceutical formulation comprising a compound of Formula I and one or more excipients.

A fourth aspect is a method of treating ischemic disease in a mammal, including a human, by administering an effective amount of a compound of Formula I.

BRIEF DESCRIPTION OF THE DRAWING

FIGURE one is a schematic demonstrating the synthesis of 2-amino-3-benzoyl-4,5-dimethylthiophenes (compounds 4–17).

DETAILED DESCRIPTION

Figure 1:
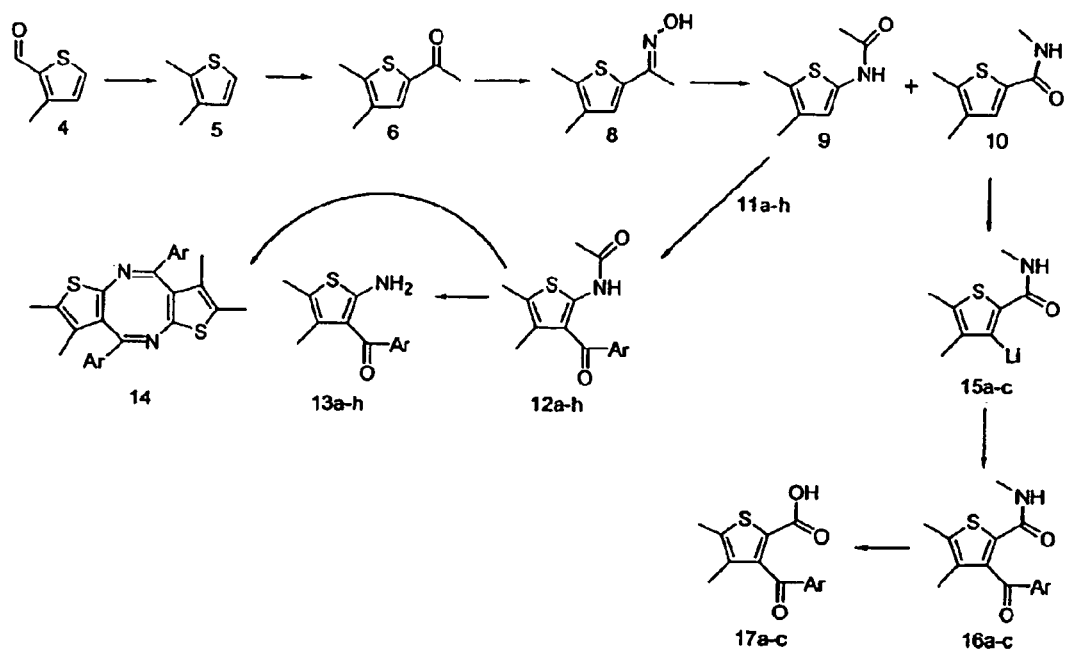

Specific compounds of the present invention are (Formula 1):

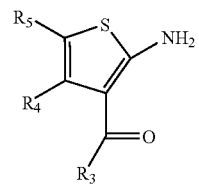

wherein:

$R_3$ is selected from the group consisting of 1-napthyl, 2-napthyl and 1-cycloalkyphenyl; and 1-naphthyl and 2-napthyl are optionally substituted with $(C_1-C_6)$alkyl groups, $(C_2-C_6)$alkenyl groups, $(C_1-C_6)$alkanoyl groups, $(C_1-C_6)$alkanoyloxy groups, $(C_3-C_6)$ cycloalkyl groups, $(C_3-C_6)$ cycloalkenyl groups, halo $(C_1-C_6)$alkyl groups, $(C_1-C_6)$alkoxy groups, $(C_1-C_6)$alkoxycarbonyl groups, $(C_3-C_6)$cycloalkyl$(C_1-C_6)$alkyl groups, $(C_2-C_6)$alkynyl groups, cyano or one of more halogen atoms, such as fluorine, chlorine, bromine or iodine; and $R_4$ and $R_5$ are taken together to form an unsaturated or saturated ring having from 5 to 10 atoms.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkenyl can be cyclopropenyl, cyclobutenyl, cyclopentenyl, or cyclohexenyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2, 2-trifluoroethyl, or pentafluoroethyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be acetoxy, propanoyloxy, butanoyloxy, isobutanoyloxy, pentanoyloxy, or hexanoyloxy. The preceding examples are illustrative, not exhaustive.

It will be appreciated by those skilled in the art that compounds of the invention having a chiral center may exist in and be isolated in optically active and racemic forms. It is to be understood that the present invention encompasses any racemic, optically-active, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine agonist or antagonist activity using the standard tests described herein, or using other similar tests which are well known in the art.

Processes for preparing compounds of Formula I or for preparing intermediates useful for preparing compounds of Formula I are provided as further embodiments of the invention. Intermediates useful for preparing compounds of Formula I are also provided as further embodiments of the invention.

In cases where compounds are sufficiently basic or acidic to form acid or base salts, use of the compounds as salts may be appropriate. Examples of acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The ability of a compound of the invention to enhance the affects of adenosine may be determined using pharmacological models well known to the art, or using the assays described herein below.

Compounds of this invention may be useful for: (1) protection against hypoxia- and/or ischemia-induced injuries (e.g., stroke, infarction); (2) treatment of adenosine-sensitive cardiac arrhythmias; (3) antinociception (i.e., analgesics); (4) anticonvulsants; (5) sleep induction, (6) treatment of chronic pain and (5) other indications for which $A_1$ agonists are used.

The amount of compound of the present invention required to be effective as an allosteric enhancer of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered.

Formulations of the present invention for medical use comprise an active compound, i.e., a compound of Formula (I) with a pharmaceutically acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of Formula (I) with a pharmaceutically acceptable carrier thereof.

The formulations include, but are not limited to, those suitable for oral, rectal, topical or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier that constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding a mixture of the powdered active compound with any suitable carrier in a suitable machine.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a. conventional carrier, e.g., cocoa butter or Witepsol S55 (trademark of Dynamite Nobel Chemical, Germany), for a suppository base.

Formulations suitable for parenteral administration conveniently comprise sterile aqueous preparation of the active compound, which is preferably isotonic with the blood of the recipient. Thus, such formulations may conveniently contain distilled water, 5% dextrose in distilled water or saline. Useful formulations also comprise concentrated solutions or solids containing the compound of Formula (I), which give a solution suitable for parental administration upon dilution with an appropriate solvent.

Topical formulations include ointments, creams, gels and lotions, which may be prepared by conventional methods known in the art of pharmacy. In addition to the ointment, cream gel, or lotion base and the active ingredient, such topical formulation may also contain preservatives, perfumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The symbols and conventions used in these examples are intended to be consistent with those used in the contemporary, international, chemical literature, for example, the Journal of the American Chemical Society and Tetrahedron.

The allosteric enhancer (AE) activity was studied at the human $A_1AR$ ($hA_1AR$) of a panel of compounds consisting of nine 2-amino-3-aroylthiophenes, (3a–i), eight 2-amino-3-benzoyl-4,5-dimethylthiophenes (13a–h), three 3-aroyl-2-carboxy-4,5-dimethylthiophenes, (17a–c), ten 2-amino-3-benzoyl-5,6-ihydro-4H-cyclopenta[b]thiophenes, (19a–I), fourteen 2-amino-3-benzoyl-4,5,6,7 tetrahyd robenzo-[b]thiophenes, (20a–n), and fifteen 2-amino-3-benzoyl-5,6,7,8 tetrahydro-4H-cyclohepta[blthiophenes, (21a–o). An in vitro assay employing the $A_1AR$ agonist $^{125}I$-$N^6$-aminobenzyladenosine ($^{125}I$-ABA) and membranes from CHO-K1 cells stably expressing the $hA_1AR$ measured, as an index of AE activity, the ability of a candidate AE to slow the dissociation of the radioligand from the $A_1AR$-G protein ternary complex.

Compounds 3a–i had little or no AE activity and compounds 13a–h had only modest activity, evidence that AE activity depended absolutely on the presence of at least a methyl group at C-4 and C-5. Compounds 17a–c lacked AE activity, suggesting the 2-amino group is essential. Polymethylene bridges linked thiophene C-4 and C-5 of compounds 19a–j, 20a–m and 21a–o. AE activity increased with the size of the —$(CH_2)_n$-bridge, n=3<n=4<n=5. The 3-carbethoxy substituents of 19a, 20a and 21a did not support AE activity, but a 3-aroyl group did. Surprisingly, 3-napthoyl and 3-cycloalkylphenyl groups had the greatest enhancing activity. Particularly, bulky (or hydrophobic) substituents at the meta and para positions of the 3-phenyl group and also 3-naphthoyl groups greatly enhanced activity. Thus, the $hA_1AR$ contains an allosteric binding site able to accommodate 3-aroyl substituents that are bulky and/or hydrophobic but not necessarily planar. A second region in the $A_1AR$ interacts constructively with alkyl substituents at thiophene C-4 and/or C-5.

Chemistry.

The reaction of 2,5-dihydroxy-1,4-dithiane (thioacetaldehyde dimer) with aroylacetonitriles gave 2-amino-3-aroylthiophenes 3a–h.

The base-catalyzed condensation of an aryl β-ketonitrile with 2-butanone to form a mixture of the E- and Z-isomers of 2-benzoyl-3-ethylcrotonitrile, followed by cyclization with sulfur is a general method for the synthesis of 2-amino-3-aroyl-4,5dimethylthiophenes. However, because only the E-isomer can react with sulfur, low yields are an inherent, disadvantage of that approach. A more efficient alternative synthesis was therefore developed proceeding from 3-methyl-2-thiophenecarboxaldehyde, 4, to generate 2-amino-3-benzoyl-4,5-dimethylthiophenes 13a–h (Scheme 1). The Huang-Minlon modification of the Wolf-Kishner reduction of 4 generated 2,3dimethylthiophene, 5. Originally, an amino function was to be introduced at C-2 by nitration of 5 and then reduction of the 4,5-dimethyl-2-nitrothiophene. Unfortunately, the nitrothiophene, 6, proved difficult to purify, and the subsequent reduction gave a tar. The instability of 2-amino-4,5-dialkylthiophenes is well known. The alternative synthesis consisted of the tin (IV) chloride-catalyzed Friedel-Crafts acylation of 5 with acetyl chloride to yield 2-acetyl-4,5-dimethylthiophene, 7. Forming the oxime, 8, and $PCl_5$-catalyzed Beckmann rearrangement of that oxime gave a mixture of 2-acetamido-4,5-dimethylthiophene, 9, a key intermediate for the synthesis of 12a–g, as well as N-methyl 2-carboxamido-4,5-dimethylthiophene, 10. Friedel-Crafts acylation of 9 by benzoyl chlorides 11a–h gave 2-acetamido-3-benzoylthiophenes 12a–h. Solvent importantly affected yield; in the case of acylation with benzoyl chloride, replacing benzene with 1,2-dichloroethane improved yield from 47% to 82%. Base-catalyzed deprotection of 12a–h gave the target thiophenes, 13a–h. Deprotection with acid catalyzed the formation of the dimers such as 14, which lacked AE activity. The dimerization was not readily apparent in NMR spectra, but was evident in high-resolution mass spectrometry. Deprotection of the 2,4,6-trimethylbenzoyl compound 12h with acid did not lead to dimerization, perhaps a result of the electronic or steric effects of the three methyl groups.

Compound 10 is a side product in the pathway leading to 13a–h, but its derivatives offered the chance to test whether the 2-amino group is important for activity. The 2-amino group was replaced with a carboxyl group, prepared by the hydrolysis of the amide group of 10. That approach failed because the electron-withdrawing effect of the 2-substituent made the thiophene resistant to Fridel-Crafts acylation at C-3. However, another approach circumvented that problem. Lithiation of 10 to lithiothiophene 15 permitted acylation with benzoyl chlorides, forming the amides, 16a–c. Alkaline hydrolysis then gave compounds 17a–c.

The method of Gewald served for the syntheses of 5,6-dihydro-4H-cyclopenta[b]thiophenes 19a–h, 4,5,6,7-tetrahydrobenzo[b]thiophenes 20a–n and 5,6,7,8-tetrahydro-4H-cyclohepta[b]thiophenes 21a–o. That method consists of the base-catalyzed condensation (Knoevenagel) of a cycloalkanone 18a–c with an aryl β-ketonitrile to form an olefin. Subsequently, that olefin undergoes cyclization with sulfur to form a 2-amino-3-aroylthiophene. Most of the present syntheses followed the "one pot" variant, which consists of adding all the reactants and catalyst at once, thereby avoiding the necessity of isolating the olefin intermediate before the subsequent reaction with sulfur. The two-step variant served for making multigram quantities of 20l and 20n. Diethylamine was usually the catalyst; however, a solid phase catalyst gave results similar to those using diethylamine. Neither LiCl, nor zeolites, which suffice for Knoevenagel condensations of aldehydes, catalyzed the condensation of ketones.

Bromoacetylarenes were the starting materials for the preparation of the β-ketonitriles used to synthesize the thiophenes. Since only a few were commercially available, they were prepared them by reacting acetoarenes with elemental bromine in glacial acetic acid, 1,4-dioxane dibromide, copper (II) bromide or tetrabutylammonium tribromide. Brominations by means of Cu(II)Br or tetrabutylammonium tribromide were rapid, clean and nearly quantitative. By contrast, brominations with either $Br_2$/acetic acid or dioxane dibromide required over two equivalents of brominating agent to drive the reaction to completion. Reacting the bromoacetylarenes with NaCN in cooled ethanol-water generated the β-ketonitriles.

Experimental Section

Melting points are uncorrected. Elemental analyses agreed within ±0.4% of calculated composition. $^1$H NMR spectra were consistent with the putative structures. Trans-World Chemicals, Rockville, Md., supplied 3'-iodoacetophenone. One recrystallization from methanol removed minor impurities from 4-acetylbiphenyl. All other starting materials were from Aldrich and were used as received. The brominations of acetylarenes and their conversions to aroylacetonitriles followed the methods cited.

2-Amino-3-benzoylthiophene (3a). A mixture of benzoylacetonitrile (1.45 g, 10 mmole), 2,5-dihydroxy-1,4-dithiane (0.76 g, 5 mmole) and diethylamine (0.73 g=1.04 mL, 10 mmole) in 4 mL absolute ethanol was heated in a teflon-sealed pressure tube for 4 hours at 50° C. with frequent stirring on a vortex mixer. By 2 hours starting materials had dissolved and shortly thereafter product began to crystallize. After refrigerating the tube overnight, the product was filtered off and washed with a little methanol to give bright yellow crystals. Yield 1.3 g, 64% $^1$H NMR (CDCl$_3$) δ: 6.14 (d, 1H, H-5), 6.88 (d, 1H, H-4), 6.95 (br s, 2H, NH$_2$), 7.75–7.7 (M, 5H, C$_6$H$_5$).

2,3-dimethylthiophene (5). Heating a mixture of 3-methyl-2-thiophene carboxaldehyde, 4 (58.6 g, 464 mmole), 80% hydrazine hydrate (97 mL, 1.62 mole) and 200 mL ethylene glycol to an internal temperature of 130–160° C. caused hydrazine and water to distil. The reaction mixture was cooled to below 60° C. and the water-immiscible fraction of the distillate was returned to the flask. The addition of KOH (91.0 g, 1.62 mole) and reheating caused vigorous gas evolution when the temperature reached 90–100° C. Reflux continued for 15 minutes after gas evolution ceased; steam distillation then separated 5. Product in the distillate was extracted into ether, the extract washed with 6N HCl, dried over CaC$_{12}$ and evaporated. Distillation over sodium gave 5 as a colorless oil, bp 139.5–140.5, yield 39.8 g, 77%. $^1$H NMR (CDCl$_3$) δ: 2.21, s, 3H, CH$_3$; 2.41, s, 3H, CH$_3$; 6.84, d, J=5.1 Hz, 1H, H-4, 7.03, d, J=5.2 Hz, 1H, H-5. $^{13}$C NMR(CDCl$_3$) δ: 13.0, 13.6, 120.6, 129.9, 132.6, 133.0.

(4,5-dimethyl-2-thienyl)(methyl) methanone (7). A solution of 5 (15.16 g, 135 mmole) and acetyl chloride (9.6 mL, 135 mmole) in 60 mL benzene dried over Na was cooled to −5° C. and vigorously stirred during the addition of a solution of tin (IV) chloride in 50 mL benzene over a period of 1 hour. The reaction mixture was removed from the cold bath and stirred for an additional hour at room temperature. The slow addition of 4 mL concentrated HCl in 28 mL water quenched the reaction. The organic layer was separated, washed with 2×10 mL water, dried over Na$_2$SO$_4$ and evaporated to give 20.8 g of crude product. Chromatography on a column of silica eluted with pet. ethenethyl acetate (10:1) and evaporation of relevant fractions gave a viscous yellow oil, 16.42 g, 79%. $^1$H NMR (CDCl$_3$) δ:2.08, s, 3H, COCH$_3$; 2.31, s, CH$_3$; 2.41, s, 3H, CH$_3$; 7.33, s, 1H, H-3. $^{13}$C NMR (CDCl$_3$) δ: 13.3, 13.7, 26.1, 134.7, 135.3, 139.1, 143.4, 190.0.

1-(4,5-dimethyl-2-thiophen-2-yl)-ethanone oxime (8). A mixture of 7 (33.1 g, 215 mmole), hydroxylamine hydrochloride (32.9 g, 473 mmole) and barium carbonate (91.7 g, 495 mmole) in 500 mL ethanol was heated at reflux for 8 hours, the salts filtered and the filtrate evaporated to an off-white solid. Crystallization from ethanol-water afforded 30.8 g (85 %) of pure 8. Four recrystallizations improved the E:Z ratio of isomers from 4:1 to 14:1. 2.11 (s, 3H, CH$_3$C=NOH), 2.26 (s, 3H, CH$_3$), 2.32 (s, 3H, CH$_3$), 6.94 (s, 1H, H-3), 9.62 (br s, 1H, OH. $^{13}$C NMR (CDCl$_3$) δ: 11.4, 12.6, 12.9, 129.2, 132.7, 133.1, 135.8, 149.4.

N-(4,5-dimethyl-thiophen-2-yl) acetamide (9) and 4,5-dimethyl-thiophene-2-carboxylic acid methylamide (10). A solution of 8 (0.304 g, 1.8 mmole) in 5 mL dry ether was cooled to 0° C. and stirred vigorously during the addition of PCl$_5$ (0.4 g, 1.9 mmole) at a rate that kept the temperature at 0° C. Stirring on ice continued for 15 min and at room temperature for an additional 30 min. The addition of 1 mL water at a rate keeping the temperature <20° C. quenched the reaction. Under cooling NaOH was added to bring the pH to 5–6, and product was extracted into ether. Evaporation gave 0.324 g of crude product that was purified by elution from a silica gel column with pet ether-ethyl acetate 1:1 to give 9 (0.097 g, 32%). $^1$H NMR (CDCl$_3$) δ: 2.03 (s, 3H, COCH$_3$), 2.16 (s, 3H, CH$_3$), 2.24 (s, 3H, CH$_3$), 6.39 (s, 1H, H-3), 9.08 (br s, 1H, NHC=O). $^{13}$C NMR (CDCl$_3$) δ: 12.3, 13.4, 23.0, 115.6, 124.8, 129.5, 134.2, 167.3. Additional fractions contained 10 (0.060 g, 20%). $^1$H NMR (CDCl$_3$) δ: 2.10 (s, 3H, C$_H$3), 2.33 (s, 3H, CH3), 2.94 (d, 3H, NHCH3), 6.21 (br s, 1H, NH, 7.22 (1H, ArH. $^{13}$C NMR (CDCl$_3$) δ: 13.4, 13.5, 26.6, 131.0, 133.2, 134.0, 138.2, 162.8.

N-(3-benzoyl-4,5-dimethyl-thiophen-2-yl)acetamide (12a). General Method A. A solution of 1.71 M tin (IV) chloride (3.1 mL, 5.3 mmole) in 1,2-dichloroethane was added dropwise to a suspension of 9 (0.241 g, 1.42 mmole) and benzoyl chloride (0.31 mL, 2.66 mmole) in 1,2-dichloroethane and the mixture was refluxed for 10.5 hours. The reaction was quenched with ice and the organic phase was washed sequentially with 2N HCl, water and 2N NaOH. Drying over CaCl$_2$ and evaporation gave a solid that was purified by chromatography on silica gel eluted with pet. ether-ethyl acetate 5:1. Recrystallization from water:gave 0.32 g of pure product as yellow crystals, 82%. $^1$H NMR (CDCl$_3$) δ: 1.6 (s, 3H, CH$_3$), 2.23.(s, 3H, CH$_3$), 2.24 (s, 3H, CH$_3$), 7.4–7.6 (m, 5H, C$_6$H$_5$), 11.1 (br s, 1H, NH.) $^{13}$C NMR (CDCl$_3$) δ: 12.4, 14.8, 23.6, 122.4, 124.7, 127.6, 128.3, 128.4, 131.9, 140.3, 146.4, 167.4, 195.0.

(2-amino-4,5-dimethyl-thiophen-3-yl)(phenyl)methanone (13a). General Method B. A solution of 12a (0.3 g, 1.1 mmole) in KOH (3.5 equivalents in methanol-water 1:1)

was refluxed for 45 minutes, evaporated and taken up in dichloromethane. The solution was washed three times with water, dried and evaporated to a solid that was recrystallized from ethanol-water as yellow crystals. Yield 0.25 g, 100%. $^1$H NMR (CDCl$_3$) δ: 1.5 (s, 3H, CH$_3$), 2.1 (s, 3H, CH$_3$), 6.4 (br s, 2H, NH$_2$), 7.2–7.5 (m, 5H, C$_6$H$_5$). $^{13}$C NMR (CDCl$_3$) δ: 12.5, 15.2, 114.9, 117.2, 127.8, 128.0, 128.8, 130.4, 141.7, 162.8, 193.0.

4,9-bis-(3-fluorophenyl)-2,3,7,8-tetramethyl-1,6-dithia-5,10-diaza-dicyclopenta [a,e]-cyclooctene (14). A solution of 12a (0.54 g, 1.86 mmole) in ethanolic 0.5 N HCl was heated at reflux for 7 hours, cooled and alkalinized with NaOH. Extracting into dichloromethane, drying and evaporation gave a solid that was purified by chromatography on silica gel eluted with pet. ether-ethyl acetate 10:1. Crystallization from ethanol-water gave orange crystals, 0.254 g, 57%. $^1$H NMR (CDCl$_3$) δ: 1.6 (s, 3H, CH$_3$), 2.3 (s, 3H, CH$_3$), 7.1–7.5 (m, 4H, C$_6$H$_4$F). $^{13}$C NMR (CDCl$_3$) δ: 13.0, 13.2, 115.4 (d, J=22.8 Hz), 118.1 (d, J=21.3 Hz), 123.5, 124.8 (d, J=2.6 Hz), 130.3, 130.7, 140.2 (d, J=7.3 Hz), 153.0, 162.8 (d, j=246.2 Hz), 169.1 (d, J=2.6 Hz). ES-MS m/z 463.1 (M+1), 485.1 (M+Na).

3-benzoyl-4,5-dimethylthiophene-2-carboxylic acid methylamide (16a). A solution of 10 (0.40 g, 2.37 mmole) in 20 mL dry THF was cooled to −70° C. and stirred during the addition of t-butyllithium (5.21 mmole). After 30 minutes of stirring benzoyl chloride (0.42 g=0.35 mL, 3 mmole) was added and the mixture was warmed to room temperature. Workup consisted of quenching the reaction with saturated aqueous NH$_4$Cl and extraction of product into ethyl acetate. The extract was dried over MgSO$_4$, evaporated and product purified by chromatography on silica gel eluted with hexane-ethyl acetate 1:1. Yield 0.356 g, 55% $^1$H NMR(CDCl$_3$) δ: 1.83 (s, 3H, CH$_3$), 2.37 (s, 3H, CH$_3$), 2.79 (d, 3H, NHCH$_3$), 6.58 (br s, 1H, NH), 7.42–7.78 (m, 5H, ArH).

3-benzoyl-4,5-dimethylthiophene-2-carboxylic acid (17a). A solution of 16a (0.281 g, 1.03 mmole) in methanol-water 1:1 containing 10% KOH was heated at reflux for 12 hours, neutralized and extracted with ethyl acetate. The solid after evaporation was crystallized from ethanol. Yield 0.19 g, 71%.

2-Amino-3-(3-bromobenzoyl)-4,5-dihydrocyclopenta[b]thiophene (19d). A mixture of sulfur (0.176 g, 5.5 mg-at), 3-bromobenzoylacetonitrile (1.35 g, 5.5 mmole) and cyclopentanone (0.463 g=0.482 mL, 5.5 mmole) in 4 ml anhydrous ethanol was heated at 50° C. in a teflon-capped pressure tube for 4 hours. Cooling overnight deposited crystalline product, which was filtered off, washed with a little cold methanol and dried TLC showed the material was pure; yield 1.2 g, 62% $^1$H NMR (CDCl$_3$) δ: 2.16 (m, 4H, H-4 and H-6), 2.65 (m, 2H, H-5), 7.07 (br s, 2H, NH$_2$), 7.3–7.6 (m, 4H, C$_6$H$_4$Br).

2-Amino-3-(4-phenylbenzoyl)-4,5,6,7-tetrahydrobenzo[b]thiophene (20l). A mixture of 4-phenylbenzoylacetonitrile (4.42 g, 0.02 mole), cyclohexanone (1.96 g=2.1 mL, 0.02 mole), β-alanine (0.18 g, 0.002 mole), glacial acetic acid (2 mL and toluene (100 mL was heated at reflux in a flask fitted with a Dean-Stark trap and condenser. After 18 hours TLC (hexane:ethyl acetate 3:1) showed complete conversion of the nitrile, Rf 0.48, to the olefin, Rf 0.67. The residue after evaporation was taken up in ethyl acetate washed twice with 50 mL water, dried over MgSO$_4$ and evaporated to a glass. Weight 4.6 g, 76%. Sulfur (0.673 g, 0.021 mole) was suspended in a solution of the olefin in 50 mL anhydrous ethanol, diethylamine. (1 mL) was added and the dark solution was stirred at room temperature until the sulfur had disappeared. Product that crystallized out on cooling in an ice bath was filtered off, washed with a little methanol and dried. TLC (hexane:ethyl acetate 1:3) showed only product, Rf 0.50. Yield 4.5 g, 67% based on starting nitrile. $^1$H NMR, δ: 1.57 (m, 2H, cyclohexyl), 1.81 (m, 2H, cyclohexyl), 1.97 (q, 2H, cyclohexyl), 2.59 (q, 2H, cyclohexyl), 6.75 (br s, 2H, NH$_2$) 7.45–7.75 (m, 9H, biphenyl).

Assay of AE Activity

The assay of AE activity consisted of three phases: formation of the $^{125}$I-ABA-A$_1$AR-G protein ternary complex; binding of the AE to the allosteric site, and dissociation of the complex by adding a combination of an A$_1$AR antagonist (100 μM cyclopentyltheophylline) and 50 PM GTPγS. This procedure detects only AE activity since phase 3 (dissociation) is affected only by the allosteric activity of the test compound and is not affected by competitive antagonist activity. GTPγS is added to accelerate the dissociation process. It was discovered that adding the guanine nucleotide did not interfere with AE activity, but reduced the time needed to accurate measure AE activity during phase 3 from hours to minutes. The assay employed membranes from CHO-K1 cells stably expressing the hA$_1$AR. For agonist binding to equilibrium, the incubation mixture consisted of 10 mM HEPES, pH 7.2, containing 0.5 mM MgCl$_2$, 1 U/mL adenosine deaminase, 0.5 nM $^{125}$I-ABA and 10 μg of membrane protein in a final volume of 100 μL. This phase of the assay was allowed to proceed to equilibrium (>90 minutes) at room temperature. At that point phase 2 was initiated by adding 50 μL of a 0.3 mM solution (0.1 mM final) of a candidate AE or DMSO vehicle to rapidly occupy the allosteric site. Stock solutions of AEs (10 mM) were prepared in DMSO. Five minutes later phase 3 was initiated by the addition of 50 μL of a solution containing 400 μM 8-cyclopentyltheophylline and 200 μM GTPγS. Ten minutes later, residual radioligand bound to A$_1$receptors was trapped on Whatman GF/C glass fiber filters using a Brandel cell harvester, washed 3 times over a 20 second interval and counted in a γ-counter. The percentage of specifically bound agonist remaining after 10 minutes of dissociation was used to calculate the "score" of AE activity:

AE activity score=100×$(B-B_o)/(B_{eq}-B_o)$

Where B=residual binding (cpm) bound at the end of 10 minutes of dissociation in the presence of an AE, B$_o$=residual binding (cpm) at the end of 10 minutes of dissociation in the absence of an AE, and B$_{eq}$=cpm bound at the end of phase 2. A compound with no AE activity has a score of 0 in this assay. An AE which completely arrests agonist dissociation will have a score of 100.

Results

The 3-aroyl moieties contributed importantly to AE activity. None of the cycloalkylthiophenes having a 3-carboxyethyl substituent, namely, 19a, 20a and 21a, was active. An unsubstituted benzoyl group supported a low level of AE activity, and both 3- and 4-fluorobenzoyl groups generally did likewise. Other benzoyl substituents increased AE activity, the rank order for all substituents being H=F<<Cl<Br<l=Ph=cHex. Both the 1- and the 2-isomers of 3-naphthoylthiophenes had substantial AE activity. QSAR analysis[15] showed that neither of the electronic parameters, σ$_m$ or σ$_p$, of the 3-phenyl substituent accounted for differences in AE activity (r$^2$ for the regressions of AE data on either Hammett parameter were <0.1 and were not significant; data not shown). However, the hydrophobic and steric parameters, π and molar refractivity, respectively, both accounted for the effect of the 3-aroyl substituents on AE activity that the analysis could not distinguish between hydrophobicity and steric bulk is not surprising, since those substituent parameters tend to be covariant. For the substituent groups studied here; $r^2$ was 0.83 for the regression of $\pi$ on molar refractivity. Although most of the 3-aroyl substituents were planar, thiophenes having 4phenylphenyl (19i, 20k, 21m) or 4-cyclohexylphenyl (20l, 21n) substituents had excellent activity.

Table 1 lists the chemical characteristics of the novel compounds. Table 2 shows the $A_1AR$ antagonistic activity of a subset of AEs, based on their ability to compete with the equilibrium binding of $[^3H]CPX$. Several of the candidate AEs had substantial antagonistic activity. However, the AE and antagonist activities are unrelated ($r^2=0.057$, n=28). Several compounds including 21h,l had very high AE activity but were nearly devoid of antagonist activity at 100 μM.

None of the compounds exerted AE activity at either the $hA_{2A}AR$ or the $hA_3AR$. Since $N^6$-substituted adenosines are agonists at both the $A_1AR$ and $A_3AR$, assigning a biological response to one or the other receptor on the basis of an agonist activity profile may give ambiguous results. Potentiation by an allosteric enhancer could be an additional criterion for deciding that the $A_1AR$ rather than the $A_3AR$ initiates a response.

TABLE 1

Characteristics of Aminothiophenes

| No | $R_3$—$R_4$—$R_5$ | Yield % | Purification | Mp ° C. | Formula | anal |
|---|---|---|---|---|---|---|
| 3a | Ph, H, H | 82 | E | 147 | $C_{11}H_9NOS$ | C,H,N |
| 3b | 3-FPh, H, H | 47 | E | 155 | $C_{11}H_8FNOS$ | C,H,N |
| 3c | 3-ClPH, H, H | 53 | E | 146 | $C_{11}H_8ClNOS$ | C,H,N |
| 3d | 3-BrPH, H, H | 56 | E | 135 | $C_{11}H_8BrNOS$ | C,H,N |
| 3e | 4-FPh, H, H | 69 | E | 143 | $C_{11}H_8FNOS$ | C,H,N |
| 3f | 4-ClPh, H, H | 47 | E | 171 | $C_{11}H_8ClNOS$ | C,H,N |
| 3g | 4-BrPh, H, H | 41 | E | 153 | $C_{11}H_8BrNOS$ | C,H,N |
| 3h | 3,4-Cl$_2$Ph, H, H | 71 | E | 139 | $C_{11}H_7C_{12}NOS$ | C,H,N |
| 3i | 2-Naph, H, H | 63 | E | 145 | $C_{15}H_{11}NOS$ | C,H,N |
| 13a | Ph, Me, Me | 100 | E | 130 | $C_{13}H_{13}NOS$ | C,H,N |
| 13b | 3-FPh, Me, Me | 54 | E | 106 | $C_{13}H_{12}FNOS$ | C,H,N |
| 13c | 3-ClPh, Me, Me | 38 | E | 115 | $C_{13}H_{12}ClNOS$ | C,H,N |
| 13d | 3-BrPh, Me, Me | 94 | E | 129 | $C_{13}H_{12}BrNOS$ | C,H,N |
| 13e | 3-CH$_3$Ph, Me, Me | 63 | E | 119 | $C_{14}H_{15}NOS$ | C,H,N |
| 13g | 3-PhPh, Me, Me | 93 | E | 162 | $C_{19}H_{17}NOS$ | C,H,N |
| 13h | Mesityl, Me, Me | 84 | E | 157 | $C_{16}H_{19}NOS$ | C,H,N |
| 17a | Ph, 2-COOH | 71 | E | 213 | $C_{13}H_{13}OS$ | C,H,N |
| 17b | 3-CF$_3$Ph, 2-COOH | 90 | E | 188 | $C_{15}H_{11}F_3O_3S$ | C,H,N |
| 17c | 4-PhPh, 2-COOH | 86 | E | 219 | $C_{20}H_{16}O_3S$ | C,H,N |
| 19a | CO$_2$Et, —(CH$_2$)$_3$— | 88 | E | 96 | $C_{10}H_{13}NO_2S$ | C,H,N |
| 19b | Ph, —(CH$_2$)$_3$— | 72 | E | 156 | $C_{14}H_{13}NOS$ | C,H,N |
| 19C | 3ClPh, —(CH$_2$)$_3$— | 59 | E | 185 | $C_{14}H_{12}ClNOS$ | C,H,N |
| 19d | 3BrPh, —(CH$_2$)$_3$— | 52 | E | 202 | $C_{14}H_{12}BrNOS$ | C,H,N |
| 19e | 4F—Ph, —(CH$_2$)$_3$— | 74 | E | 152 | $C_{14}H_{12}FNOS$ | C,H,N |
| 19f | 4-ClPh, —(CH$_2$)$_3$— | 72 | E | 125 | $C_{14}H_{12}ClNOS$ | C,H,N |
| 19g | 4BrPh, —(CH$_2$)$_3$— | 61 | E | 163 | $C_{14}H_{12}BrNOS$ | C,H,N |
| 19h | 4PhPh, —(CH$_2$)$_3$— | 31 | E | 137 | $C_{20}H_{17}NOS$ | C,H,N |
| 19i | 2-Naph, —(CH$_2$)$_3$— | 55 | E | 155 | $C_{15}H_{11}NOS$ | C,H,N |
| 20a | CO$_2$Et, —(CH$_2$)$_4$— | 73 | E | 96 | $C_{11}H_{15}NO_2S$ | C,H,N |
| 20b | Ph, —(CH$_2$)$_4$— | 64 | H | 143 | $C_{15}H_{15}NOS$ | C,H,N |
| 20c | 3-FPh, —(CH$_2$)$_4$— | 52 | H | 113 | $C_{15}H_{14}FNOS$ | C,H,N |
| 20d | 3-ClPh, —(CH$_2$)$_4$— | 22 | H | 132 | $C_{15}H_{14}ClNOS$ | C,H,N |
| 20e | 3-BrPH, —(CH$_2$)$_4$— | 37 | H | 120 | $C_{15}H_{14}BrNOS$ | C,H,N |
| 20f | 4-FPh, —(CH$_2$)$_4$— | 84 | H | 128 | $C_{15}H_{14}FNOS$ | C,H,N |
| 20g | 4-ClPh, —(CH$_2$)$_4$— | 86 | E | 138 | $C_{15}H_{14}ClNOS$ | C,H,N |
| 20h | 4-BrPh, —(CH$_2$)$_4$— | 36 | E | 130 | $C_{15}H_{14}BrNOS$ | C,H,N |
| 20i | 4-IPh, —(CH$_2$)$_4$— | 12 | E | 128 | $C_{15}H_{14}INOS$ | C,H,N |
| 20j | 4-CH$_3$Ph, —(CH$_2$)$_4$— | 79 | E | 139 | $C_{16}H_{17}NOS$ | C,H,N |
| 20k | 4-CNPh, —(CH$_2$)$_4$— | 32 | E | 209 | $C_{16}H_{14}N_2OS$ | C,H,N |
| 20l | 4-PhPh, —(CH$_2$)$_4$— | 14 | E | 110 | $C_{21}H_{19}NOS$ | C,H,N |
| 20m | 4-cHexPh, —(CH$_2$)$_4$— | 23 | E | 115 | $C_{21}H_{25}NOS$ | C,H,N |
| 20n | 2-Nap, —(CH$_2$)$_4$— | 18 | H | 105 | $C_{19}H_{17}NOS$ | C,H,N |
| 21a | CO$_2$Et, —(CH$_2$)$_5$— | 75 | E | 117 | $C_{12}H_{17}NO_2S$ | C,H,N |
| 21b | Ph, —(CH$_2$)$_5$— | 44 | E | 94 | $C_{16}H_{17}NOS$ | C,H,N |
| 21c | 3ClPh, —(CH$_2$)$_5$— | 21 | E | 75 | $C_{16}H_{16}ClNOS$ | C,H,N |
| 21d | 3-BrPh, —(CH$_2$)$_5$— | 28 | E | 81 | $C_{16}H_{16}BrNOS$ | C,H,N |
| 21e | 3-Iph, —(CH$_2$)$_5$— | 38 | E | 100 | $C_{16}H_{16}INOS$ | C,H,N |
| 21f | 4FPh, —(CH$_2$)$_5$— | 28 | H | 79 | $C_{16}H_{16}FNOS$ | C,H,N |
| 21g | 4ClPh, —(CH$_2$)$_5$— | 33 | H | 98 | $C_{16}H_{16}ClNOS$ | C,H,N |
| 21h | 4BrPh, —(CH$_2$)$_5$— | 26 | E | 154 | $C_{16}H_{16}BrNOS$ | C,H,N |
| 21i | 4-IPh, —(CH$_2$)$_5$— | 64 | E | 177 | $C_{16}H_{16}INOS$ | C,H,N |
| 21j | 3-CH$_3$OPH, —(CH$_2$)$_5$— | 30 | E | 72 | $C_{17}H_{19}NO_2S$ | C,H,N |
| 21k | 4-CH$_3$OPh, —(CH$_2$)$_5$— | 84 | E | 125 | $C_{17}H_{19}NO_2S$ | C,H,N |
| 21l | 4-PhPh, —(CH$_2$)$_5$— | 42 | E | 56 | $C_{21}H_{21}NOS$ | C,H,N |
| 21m | 4-cHxPh, —(CH$_2$)$_5$— | 31 | E | 132 | $C_{21}H_{27}NOS$ | C,H,N |
| 21n | 1-Naph, —(CH$_2$)$_5$— | 20 | E | 93 | $C_{19}H_{19}NOS$ | C,H,N |
| 21o | 2-Naph, —(CH$_2$)$_5$— | 34 | E | 121 | $C_{19}H_{19}NOS$ | C,H,N |

TABLE 2

Summary of Allosteric Enhancer Activity

| No | AE Score, %[a] | Antagonist activity, %[b] |
|---|---|---|
| 3a | 0.2 ± 0.01 | 24 |
| 3b | 0 | |
| 3c | 0 | |
| 3d | 0.2 ± 0.03 | |
| 3e | 0 | |
| 3f | 0 | |
| 3g | 0.8 ± 0.3 | |
| 3h | 1.7 ± 0.8 | |
| 3i | 3.2 ± 1.8 | |
| 13a | 9 | |
| 13b | 0 | |
| 13c | 14 ± 1 | |
| 13d | 16 ± 4 | |
| 13e | 18 ± 0.5 | |
| 13f | 19 ± 2.9 | 42 |
| 13g | 12 ± 1.9 | |
| 13h | 0 | |
| 17a | 0 | |
| 17b | 0 | |
| 17c | 0 | |
| 19a | 0.4 ± 0.1 | 72 |
| 19b | 20 ± 3.6 | 63 |
| 19c | 16 ± 2 | |
| 19d | 13 ± 3 | 76 |
| 19e | 68 ± 1 | 36 |
| 19f | 22 ± 4 | 40 |
| 19g | 70 ± 7 | |
| 19h | 62 ± 5 | 12 |
| 19i | 38 ± 3 | |
| 19j | 31 ± 4 | 23 |
| 20a | 3.5 ± 1.8 | 57 |
| 20b | 19 ± 5 | 35 |
| 20c | 22 ± 5 | 40 |
| 20d | 70 ± 9 | 2 |
| 20e | 49 ± 1 | |
| 20f | 17 ± 3 | 51 |
| 20g | 68 ± 10 | 9 |
| 20h | 83 ± 5 | 56 |
| 20i | 86 ± 13 | 31 |
| 20j | 19 ± 7 | 41 |
| 20k | 19 ± 0.9 | 19 |
| 20l | 33 ± 2 | |
| 20m | 99 ± 6 | 45 |
| 20n | 86 ± 1 | |
| 21a | 0.3 ± 0.01 | 41 |
| 21b | 13 ± 3.8 | 0 |
| 21c | 65 ± 8 | 9 |
| 21d | 78 ± 2.6 | 12 |
| 21e | 86 ± 9 | |
| 21f | 22 ± 2.7 | |
| 21g | 65 ± 6.7 | |
| 21h | 86 ± 3.8 | 12 |
| 21i | 96 ± 4.7 | 11 |
| 21j | 99 ± 3.1 | 19 |
| 21k | 85 ± 10 | |
| 21l | 88 ± 4.6 | |
| 21m | 77 ± 11 | |
| 21n | 81 ± 7.2 | |
| 21o | 75 ± 9.6 | |

[a]See the text for a description of "score." Mean ± SEM (N = 3).
[b]% inhibition of specific equilibrium binding of [$^3$H]8-cyclopentyl-1,3-dipropylxanthine, N = 3.

Many improvements, modifications, and additions will be apparent to the skilled artisan without departing from the spirit and scope of the present invention as described herein and defined in the following claims.

We claim:

1. A pharmaceutical formulation comprising a compound of the formula (I):

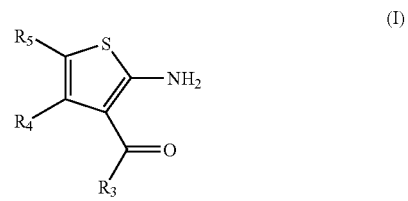

wherein:

$R_3$ is cycloalkylphenyl; and $R_4$ and $R_5$ are taken together to form a ring having 5 to 10 carbon atoms.

2. The pharmaceutical formulation of claim 1, wherein said cycloalkyphenyl is cyclohexylphenyl.

3. A pharmaceutical formulation comprising a compound of the formula (I):

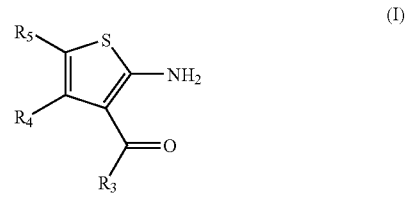

wherein:

$R_3$ is selected from the group consisting of 1-napthyl, 2-napthyl and cycloalkylphenyl; and $R_4$ and $R_5$ are taken together to form a ring having 5 to 10 carbon atoms, wherein said 1-napthyl and 2-napthyl are substituted with one or more ($C_1$–$C_6$)alkyl groups, ($C_2$–$C_6$)alkenyl groups, ($C_1$–$C_6$)alkanoyl groups, ($C_1$–$C_6$)alkanoyloxy groups, ($C_3$–$C_6$)cycloalkyl groups, ($C_3$–$C_6$)cycloalkenyl groups, halo($C_1$–$C_6$)alkyl groups, ($C_1$–$C_6$)alkoxy groups, ($C_1$–$C_6$)alkoxycarbonyl groups, ($C_3$–$C_6$)cycloalkyl($C_1$–$C_6$)alkyl groups, ($C_2$–$C_6$)alkynyl groups or halogens.

4. The pharmaceutical formulation of claim 1, wherein said ring has 5 carbon atoms.

5. The pharmaceutical formulation of claim 3, wherein said ring has 5 carbon atoms.

* * * * *

UNITED STATES PATENT AND TRADEMARK OFFICE
CERTIFICATE OF CORRECTION

PATENT NO. : 7,019,027 B2  
APPLICATION NO. : 10/808093  
DATED : March 28, 2006  
INVENTOR(S) : Joel M. Linden, Ray A. Ollson and Peter J. Scammells Page 1 of 1

It is certified that error appears in the above-identified patent and that said Letters Patent is hereby corrected as shown below:

Title Page, under Inventors, "Ray A. Ollson" should read --Ray A. Olsson--.

Signed and Sealed this

Twenty-fifth Day of July, 2006

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 7,019,027 B2 |
| APPLICATION NO. | : 10/808093 |
| DATED | : March 28, 2006 |
| INVENTOR(S) | : Joel Linden, Ray A. Ollson and Peter J. Scammells |

It is certified that error appears in the above-identified patent and that said Letters Patent is hereby corrected as shown below:

In the Specifications:

Column 1, following line 10, please insert new section -- Statement of Government License Rights This invention was made through the support of the National Institutes of Health (Grant No. RO1 HL056111). The Federal Government has certain rights in this invention. --

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,019,027 B2
APPLICATION NO.   : 10/808093
DATED             : March 28, 2006
INVENTOR(S)       : Linden et al.

Page 1 of 1

It is certified that error appears in the above-identified patent and that said Letters Patent is hereby corrected as shown below:

In column 1, line 13, after "2001.", insert --¶STATEMENT OF GOVERNMENT INTEREST
This invention was made with government support under HL056111 awarded by the National
Institutes of Health. The government has certain rights in the invention.--, therefor Signed and Sealed this
Twenty-fourth Day of May, 2016

Michelle K. Lee
*Director of the United States Patent and Trademark Office*